US 11,220,673 B2

(12) United States Patent
Zhu et al.

(10) Patent No.: US 11,220,673 B2
(45) Date of Patent: *Jan. 11, 2022

(54) ORF7 DEFICIENT VARICELLA VIRUS, VACCINE COMPRISING THE VIRUS AND USE THEREOF

(71) Applicants: Beijing Wantai Biological Pharmacy Enterprise Co., Ltd., Beijing (CN); Rutgers, the State University of New Jersey, Piscataway, NJ (US); Xiamen University, Fujian Province (CN)

(72) Inventors: Hua Zhu, Newark, NJ (US); Yimin Li, Beijing (CN); Ningshao Xia, Fujian Province (CN); Tong Cheng, Fujian Province (CN); Xiangzhong Ye, Beijing (CN)

(73) Assignees: Beijing Wantai Biological Pharmacy Enterprise Co., Ltd., Beijing (CN); Rutgers, The State University of New Jersey, Piscataway, NJ (US); Xiamen University, Fujian Province (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/847,360

(22) Filed: Apr. 13, 2020

(65) Prior Publication Data
US 2020/0277577 A1    Sep. 3, 2020

Related U.S. Application Data

(60) Continuation of application No. 15/865,540, filed on Jan. 9, 2018, now Pat. No. 10,752,885, which is a division of application No. 13/387,359, filed as application No. PCT/CN2010/001139 on Jul. 27, 2010, now Pat. No. 9,885,020.

(51) Int. Cl.
| | |
|---|---|
| *C12N 7/00* | (2006.01) |
| *A61K 39/25* | (2006.01) |
| *C07K 14/005* | (2006.01) |
| *A61K 39/12* | (2006.01) |
| *C12N 15/86* | (2006.01) |
| *A61K 39/00* | (2006.01) |

(52) U.S. Cl.
CPC .............. *C12N 7/00* (2013.01); *A61K 39/12* (2013.01); *A61K 39/25* (2013.01); *C07K 14/005* (2013.01); *C12N 15/86* (2013.01); *A61K 2039/5254* (2013.01); *C12N 2710/16722* (2013.01); *C12N 2710/16734* (2013.01)

(58) Field of Classification Search
None
See application file for complete search history.

(56) References Cited

U.S. PATENT DOCUMENTS

| | | | |
|---|---|---|---|
| 5,607,852 A | 3/1997 | Provost | |
| 9,885,020 B2 | 2/2018 | Zhu | |
| 10,752,885 B2 * | 8/2020 | Zhu | A61K 39/12 |

FOREIGN PATENT DOCUMENTS

| | | |
|---|---|---|
| CN | 1950507 A | 4/2007 |
| EP | 1721981 | 11/2006 |
| WO | 2004042031 A2 | 5/2004 |
| WO | 2005/085445 A1 | 9/2005 |

OTHER PUBLICATIONS

Chinese Office Action dated Sep. 30, 2014 for Appln. No. 2012-521930.
Zhang et al., "A highly efficient protocol of generating and analyzing VZV ORF deletion mutants based on a newly developed luciferase VZV BAC system", Journal of Virological Methods, 2008, vol. 148, pp. 197-204.
Warming et al., "Simple and highly efficient BAC recombineering using galK selection", Nucleic Aids Research, 2005, vol. 33, No. 4, pp. 17-28.
Cheng et al., "OFR7 of Varicella-Zoster Virus is a Neutrotropic Factor", Journal of Virology, Aug. 2012, vol. 86, No. 16, 12 pgs.
Zhang et al., "Genome-Wide Mutagenesis Reveals That ORF7 is a Novel VZV Skin-Tropic Factor", PLOS Pathogens; 2010, vol. 6, Issue 7, pp. 1-9.
Zhang et al., "Genetic Analysis of Varicella-Zoster virus ORF0 to ORF4 by Use of a Novel Luciferase Bacterial Artificial Chromosome System", Journal of Virology, 2007, vol. 81, No. 17, pp. 9024-9033.
Australian Office Action dated Jun. 3, 2015 for Appln. No. 2010278594.
CDC—Chickenpox or Varicella Zoster Virus Fact Sheet for Parents—Vaccines 2014, downloaded http://www.cdc.gov/vaccines/vpd-vac/varicella/fs-parents.html.
CDC—Shingles Vaccination—Herpes Zoster, 2014, downloaded http://www.cdc.gov/shingles/vaccination.html.
Papaloukas et al., "Successes and challenges in varicella vaccine" 2014, Therapeutic Advances in Vaccines, vol. 2, No. 2, pp. 39-55.
Niizuma et al., Construction of Varicella-Zoster Virus Recombinants from Parent Oka Cosmids and Demonststration that ORF65 Protein is Dispensable for Infection of Human Skin and T Cells in the SCID-hu Mouse Model, 2003, Journal of Virology, vol. 77, No. 10, pp. 6062-6065.
European Office Action dated Oct. 8, 2013 for Appln. No. 10 803 804.2-1410.
International Search Report as issued in PCT/CN010/001139 dated Nov. 4, 2010 (5 pgs.).
Z. Zhang et al., "A highly efficient protocol of generating and analyzing VZV ORF deletion mutants based on a newly developed luciferase VZV BAC system", J. of Virological Methods, vol. 148, Nos. 1-2, pp. 197-204 (Jan. 2008).

(Continued)

*Primary Examiner* — Benjamin P Blumel
(74) *Attorney, Agent, or Firm* — Pillsbury Winthrop Shaw Pittman LLP

(57) ABSTRACT

Provided are an ORF7 deficient varicella virus, an vaccine comprising the virus and use thereof, as well as a method for the production the virus.

5 Claims, 11 Drawing Sheets

Specification includes a Sequence Listing.

(56) References Cited

OTHER PUBLICATIONS

P. Kennedy et al., "Transcriptomal analysis of varicell-zoster virus infection using long oligonucleotide-based microarrays", J. of General Virology, vol. 86, pp. 2673-2684 (Oct. 2005).
Moffat et al., "Glycoprotein I of Varicella-Zoster Virus Is Required for Viral Replication in Skin and T. Cells", Journal of Virology, 2002, vol. 76, No. 16, pp. 8468-8471.
European Office Action dated Oct. 8, 2013 for Appln. No. 10 803 804.3-1410.
European Office Action dated Apr. 29, 2014 for Appln. No. 10 803 804.3-1410.
Notice of Allowance issued in corresponding U.S. Appl. No. 15/865,540 dated Apr. 6, 2020 (10 pages).

\* cited by examiner

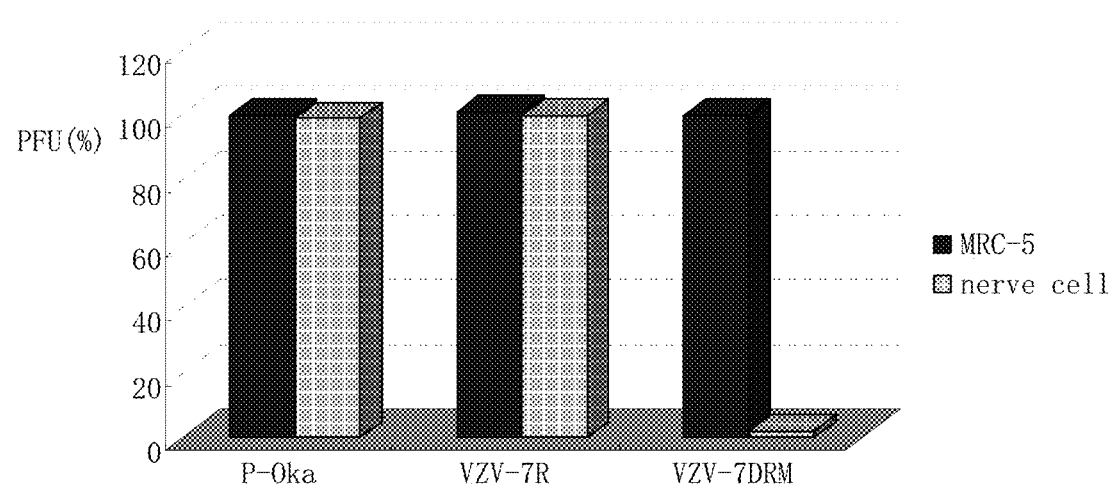
Fig.9 ( A )

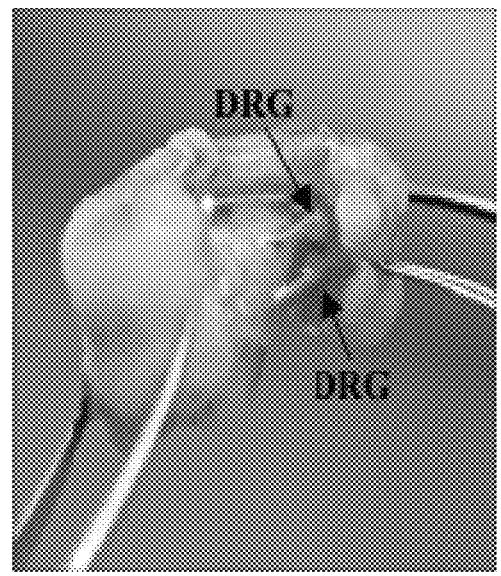
Fig.9 ( B )
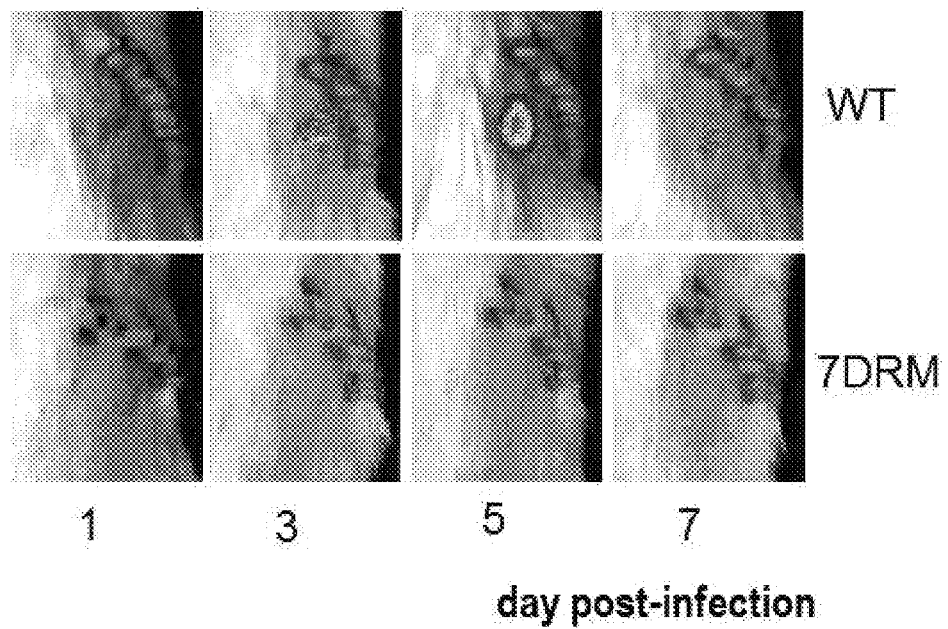
Fig.9 ( C )

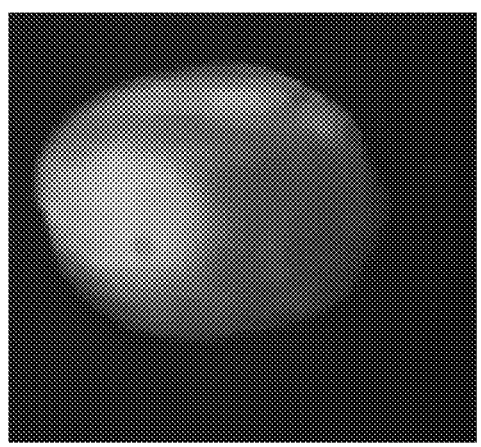
Fig.9 ( D )

SEQUENCE LISTING

<160> NUMBER OF SEQ ID NOS: 18

<210> SEQ ID NO 1
<211> LENGTH: 780
<212> TYPE: DNA
<213> ORGANISM: varicella virus P-Oka strain

<400> SEQUENCE: 1

```
atgcagacgg tgtgtgccag cttatgtgga tatgctcgaa taccaactga agagccatct      60
tatgaagagg tgcgtgtaaa cacgcacccc caaggagccg ccctgctccg cctccaagag     120
gctttaaccg ctgtgaatgg attattgcct gcacctctaa cgttagaaga cgtagtcgct     180
tctgcagata atacccgtcg tttggtccgc gcccaggctt ggcgcgaac ttacgctgca      240 tgttctcgta acattgaatg tttaaaacag caccatttta ctgaagataa ccccggtctt     300
aacgccgtgg tccgttcaca catggaaaac tcaaaacggc ttgctgatat gtgtttagct     360
gcaattaccc atttgtattt atcggttggc gcggtggatg ttactacgga tgatattgtc     420
gatcaaaccc tgagaatgac cgctgaaagt gaagtggtca tgtctgatgt tgttcttttg     480
gagaaaactc ttggggtcgt tgctaaacct caggcatcgt tgatgtttc ccacaaccat      540 gaattatcta tagctaaagg ggaaaatgtg ggtttaaaaa catcacctat taaatcggag     600
gcgacacaat tatctgaaat taaaccccca cttatagaag tatcggataa taacacatct     660
aacctaacaa aaaaaacgta tccgacagaa actcttcagc ccgtgttgac cccaaaacag     720
acgcaagatg tacaacgcac aaccccgcg atcaagaaat cccatgttat gcttgtataa     780
```

<210> SEQ ID NO 2
<211> LENGTH: 816
<212> TYPE: DNA
<213> ORGANISM: artifical sequence
<220> FEATURE:
<223> OTHER INFORMATION: Kanr gene

<400> SEQUENCE: 2

```
atgagccata ttcaacggga aacgtcttgc tcgaggccgc gattaaattc caacatggat      60
gctgatttat atgggtataa atgggctcgc gataatgtcg ggcaatcagg tgcgacaatc     120
tatcgattgt atgggaagcc cgatgcgcca gagttgtttc tgaaacatgg caaaggtagc     180
gttgccaatg atgttacaga tgagatggtc agactaaaact ggctgacgga atttatgcct     240
cttccgacca tcaagcattt tatccgtact cctgatgatg cgtggttact caccactgcg     300
atccccggaa aaacagcatt ccaggtatta gaagaatatc ctgattcagg tgaaaatatt     360
gttgatgcgc tggcagtgtt cctgcgccgg ttgcattcga ttcctgtttg taattgtcct     420
```

```
tttaacagcg atcgcgtatt tcgtctcgct caggcgcaat cacgaatgaa taacggtttt    480
gttgatgcga gtgattttga tgacgagcat aatggctggc ctgttgaaca agtctggaaa    540
gaaatgcata aacttttgcc attctcaccg gattcagtcg tcactcatgg tgatttctca    600
cttgataacc ttattttga cgaggggaaa ttaataggtt gtattgatgt tggacgagtc    660
ggaatcgcag accgatacca ggatcttgcc atcctatgga actgcctcgg tgagttttct    720
ccttcattac agaaacggct ttttcaaaaa tatggtattg ataatcctga tatgaataaa    780
ttgcagtttc atttgatgct cgatgagttt ttctaa                             816
```

```
<210> SEQ ID NO 3
<211> LENGTH: 61
<212> TYPE: DNA
<213> ORGANISM: artifical sequence
<220> FEATURE:
<223> OTHER INFORMATION: primer F1

<400> SEQUENCE: 3
gatttatcca tagttcaata cgttggaaag ccagtcaatc gctcttgttg ctagtgcgt    60 a                                                                   61
```

```
<210> SEQ ID NO 4
<211> LENGTH: 60
<212> TYPE: DNA
<213> ORGANISM: artifical sequence
<220> FEATURE:
<223> OTHER INFORMATION: primer R1

<400> SEQUENCE: 4
aaacatacac cagaaacgtt tttagttttt atttcaatat tctgccagtg ttacaaccaa    60
```

```
<210> SEQ ID NO 5
<211> LENGTH: 1231
<212> TYPE: DNA
<213> ORGANISM: artifical sequence
<220> FEATURE:
<223> OTHER INFORMATION: galk gene

<400> SEQUENCE: 5
cctgttgaca attaatcatc ggcatagtat atcggcatag tataatacga caaggtgagg    60
aactaaaccc aggaggcaga tcatgagtct gaaagaaaaa acacaatctc tgtttgccaa    120
cgcatttggc taccctgcca ctcacaccat tcaggcgcct ggccgcgtga atttgattgg    180
tgaacacacc gactacaacg acggtttcgt tctgccctgc gcgattgatt atcaaaccgt    240
gatcagttgt gcaccacgcg atgaccgtaa agttcgcgtg atggcagccg attatgaaaa    300
tcagctcgac gagttttccc tcgatgcgcc cattgtcgca catgaaaact atcaatgggc    360
taactacgtt cgtggcgtgg tgaaacatct gcaactgcgt aacaacagct cggcggcgt     420 ggacatggtg atcagcggca atgtgccgca gggtgccggg ttaagttctt ccgcttcact    480
ggaagtcgcg gtcggaaccg tattgcagca gctttatcat ctgccgctgg acggcgcaca    540
aatcgcgctt aacggtcagg aagcagaaaa ccagtttgta ggctgtaact gcgggatcat    600
ggatcagcta atttccgcgc tcggcaagaa agatcatgcc ttgctgatcg attgccgctc    660
actggggacc aaagcagttt ccatgcccaa aggtgtggct gtcgtcatca tcaacagtaa    720
cttcaaacgt accctggttg gcagcgaata caaccacccgt cgtgaacagt gcgaaaccgg    780
tgcgcgtttc ttccagcagc cagccctgcg tgatgtcacc attgaagagt tcaacgctgt    840
```

-continued

```
tgcgcatgaa ctggacccga tcgtggcaaa acgcgtgcgt catatactga ctgaaaacgc      900
ccgcaccgtt gaagctgcca gcgcgctgga gcaaggcgac ctgaaacgta tgggcgagtt      960
gatggcggag tctcatgcct ctatgcgcga tgatttcgaa atcaccgtgc cgcaaattga     1020
cactctggta gaaatcgtca aagctgtgat tggcgacaaa ggtggcgtac gcatgaccgg     1080
cggcggattt ggcggctgta tcgtcgcgct gatcccggaa gagctggtgc ctgccgtaca     1140
gcaagctgtc gctgaacaat atgaagcaaa aacaggtatt aaagagactt tttacgtttg     1200
taaaccatca caaggagcag acagtgctg a                                    1231
```

<210> SEQ ID NO 6
<211> LENGTH: 87
<212> TYPE: DNA
<213> ORGANISM: artifical sequence
<220> FEATURE:
<223> OTHER INFORMATION: primer F2

<400> SEQUENCE: 6

```
accgaatcgt cggtttggag gatttatcca tagttcaata cgttggaaag ccagtcaatc       60
atgcctgttg acaattaatc atcggca                                         87
```

<210> SEQ ID NO 7
<211> LENGTH: 80
<212> TYPE: DNA
<213> ORGANISM: artifical sequence
<220> FEATURE:
<223> OTHER INFORMATION: primer R2

<400> SEQUENCE: 7

```
taattttata tacaaaataa aaacatacac cagaaacgtt tttagttttt atttcaatat       60
tcagcactgt cctgctcctt                                                 80
```

<210> SEQ ID NO 8
<211> LENGTH: 24
<212> TYPE: DNA
<213> ORGANISM: artifical sequence
<220> FEATURE:
<223> OTHER INFORMATION: primer F3

<400> SEQUENCE: 8

```
cctgttgaca attaatcatc ggca                                            24
```

<210> SEQ ID NO 9
<211> LENGTH: 20
<212> TYPE: DNA
<213> ORGANISM: artifical sequence
<220> FEATURE:
<223> OTHER INFORMATION: primer R3

<400> SEQUENCE: 9

```
tcagcactgt cctgctcctt                                                 20
```

<210> SEQ ID NO 10
<211> LENGTH: 82
<212> TYPE: DNA
<213> ORGANISM: artifical sequence
<220> FEATURE:
<223> OTHER INFORMATION: primer F4

<400> SEQUENCE: 10

```
cgaatcgtcg gtttggagga tttatccata gttcaatacg ttggaaagcc agtcaattta       60
atgggatttc ttgatcgcgg gg                                              82
```

<210> SEQ ID NO 11
<211> LENGTH: 83
<212> TYPE: DNA
<213> ORGANISM: artifical sequence
<220> FEATURE:
<223> OTHER INFORMATION: primer R4

<400> SEQUENCE: 11
aattttatat acaaaataaa aacatacacc agaaacgttt ttagtttttta tttcaatatg    60 tggtccgttc acacatggaa aac                                             83

<210> SEQ ID NO 12
<211> LENGTH: 457
<212> TYPE: DNA
<213> ORGANISM: artifical sequence
<220> FEATURE:
<223> OTHER INFORMATION: Open Reading Frame (ORF)

<400> SEQUENCE: 12
gtccgttcac acatggaaaa ctcaaaacgg cttgctgata tgtgtttagc tgcaattacc    60
catttgtatt tatcggttgg cgcggtggat gttactacgg atgatattgt cgatcaaacc   120
ctgagaatga ccgctgaaag tgaagtggtc atgtctgatg ttgttctttt ggagaaaact   180
cttggggtcg ttgctaaacc tcaggcatcg tttgatgttt cccacaacca tgaattatct   240
atagctaaag gggaaaatgt gggtttaaaa acatcaccta ttaaatcgga ggcgacacaa   300
ttatctgaaa ttaaaccccc acttatagaa gtatcggata taacacatc taacctaaca    360 aaaaaaacgt atccgacaga aactcttcag cccgtgttga ccccaaaaca gacgcaagat   420
gtacaacgca caaccccgc gatcaagaaa tcccatg                              457

<210> SEQ ID NO 13
<211> LENGTH: 457
<212> TYPE: DNA
<213> ORGANISM: artifical sequence
<220> FEATURE:
<223> OTHER INFORMATION: flip reverse framshift mutation sequence

<400> SEQUENCE: 13
catgggattt cttgatcgcg ggggttgtgc gttgtacatc ttgcgtctgt tttggggtca    60
acacgggctg aagagtttct gtcggatacg ttttttttgt taggttagat gtgttattat   120
ccgatacttc tataagtggg ggtttaattt cagataattg tgtcgcctcc gatttaatag   180
gtgatgtttt taaacccaca ttttcccctt tagctataga taattcatgg ttgtgggaaa   240
catcaaacga tgcctgaggt ttagcaacga ccccaagagt tttctccaaa agaacaacat   300
cagacatgac cacttcactt tcagcggtca ttctcagggt tgatcgaca atatcatccg    360 tagtaacatc caccgcgcca accgataaat acaaatgggt aattgcagct aaacacatat   420
cagcaagccg ttttgagttt tccatgtgtg aacggac                             457

<210> SEQ ID NO 14
<211> LENGTH: 60
<212> TYPE: DNA
<213> ORGANISM: artifical sequence
<220> FEATURE:
<223> OTHER INFORMATION: primer F5

<400> SEQUENCE: 14
gatttatcca tagttcaata cgttggaaag ccagtcaatc atgcagacgg tgtgtgccag    60

<210> SEQ ID NO 15
<211> LENGTH: 60
<212> TYPE: DNA
<213> ORGANISM: artifical sequence
<220> FEATURE:
<223> OTHER INFORMATION: primer R5

<400> SEQUENCE: 15
aaacatacac cagaaacgtt tttagttttt atttcaatat ggatggatcc ataacttcgt 60

<210> SEQ ID NO 16
<211> LENGTH: 896
<212> TYPE: DNA
<213> ORGANISM: artifical sequence
<220> FEATURE:
<223> OTHER INFORMATION: EV71-VP1 Cassette sequence

<400> SEQUENCE: 16
tgggagatag ggtagcagat gtaattgaaa gctccatagg agatagcgtg agcagagccc 60
tcactcacgc tctaccagca cccacaggcc agaacacaca ggtgagcagt catcaactgg 120
atacaggcaa ggttccagca ctccaagctg ctgaaattgg agcatcatca aatgctagtg 180
acgagagcat gattgagaca cgctgtgttc ttaactcgca cagcacagct gagaccactc 240
ttgatagttt cttcagcaga gcgggattag ttggagagat agatctccct cttaaaggca 300
caactaaccc aaatggttat gccaactggg acatagatat aacaggttac gcgcaaatgc 360
gtagaaaggt ggagctattc acctacatgc gctttgatgc agagttcact tttgttgcgt 420
gcacacccac cggggaagtt gtcccacaat tgctccaata tatgtttgtg ccacctggag 480
cccctaagcc agattccagg gaatccctcg catggcaaac cgccaccaac ccctcggttt 540
ttgtcaagct gtcagaccct ccagcgcagg tttcagtgcc attcatgtca cctgcgagcg 600
cttaccaatg gttttatgac ggatatccca cattcggaga acacaaacag gagaaagatc 660
ttgaatatgg ggcatgtcct aataacatga tgggcacgtt ctcagtgcgg actgtaggga 720
cctccaagtc caagtaccct ttagtggtta ggatttacat gagaatgaag cacgttaggg 780
cgtggatacc tcgcccgatg cgtaaccaga actacctatt caaagccaac ccaaattatg 840
ctggcaactc cattaagcca actggtacca gtcgtacagc gatcactact ctttaa 896

<210> SEQ ID NO 17
<211> LENGTH: 83
<212> TYPE: DNA
<213> ORGANISM: artifical sequence
<220> FEATURE:
<223> OTHER INFORMATION: primer F6

<400> SEQUENCE: 17
cgaatcgtcg gtttggagga tttatccata gttcaatacg ttggaaagcc agtcaatcat 60
gggagatagg gtagcagatg taa 83

<210> SEQ ID NO 18
<211> LENGTH: 90
<212> TYPE: DNA

```
<213> ORGANISM: artifical sequence
<220> FEATURE:
<223> OTHER INFORMATION: primer R6

<400> SEQUENCE: 18
aattttatat acaaaataaa aacatacacc agaaacgttt ttagttttta tttcaatatt        60
taaagagtag tgatcgctgt acgactggta                                        90
```

ORF7 DEFICIENT VARICELLA VIRUS, VACCINE COMPRISING THE VIRUS AND USE THEREOF

CROSS-REFERENCE TO RELATED APPLICATIONS

This application is a Continuation Application of U.S. Ser. No. 15/865,540, filed Jan. 9, 2018, which is a Divisional Application of U.S. Ser. No. 13/387,359, filed Jan. 26, 2012, now U.S. Pat. No. 9,885,020, which is the U.S. National Phase of PCT/CN2010/001139, filed Jul. 27, 2010, which in turn claims priority to Chinese Patent Application No. 200910157387.0, filed Jul. 28, 2009. The contents of each of these applications are incorporated herein by reference in entirety.

FIELD OF THE INVENTION

The present invention belongs to the field of virology and biopharmaceutical. Specifically, the invention provides ORF7-deficient varicella virus, vaccine containing the virus and its use. The invention provides a candidate vaccine for the prevention of the varicella-zoster virus.

BACKGROUND OF THE INVENTION

Varicella-zoster virus (referred to as "varicella virus" or "VZV") is a strictly species-specific virus, which is a pathogenicity factor that causes varicella or herpes zoster in human. The P-Oka strain of varicella virus was first isolated by Takahashi in 1971 from vesicles fluids of a 3 year-old Japanese boy of the surname Oka who has typical varicella and was obtained through passage of the virus in human embryonic lung cells. It is considered that the P-Oka has the capability of causing varicella and herpes zoster (Takahashi M, Otsuka T, Okuno Y, et al., Live vaccine used to prevent the spread of varicella in children in hospital. Lancet 1974; 2: 1288-90.).

It was disclosed in U.S. Pat. No. 3,985,615 that attenuated P-Oka strain is obtained by serial passaging of the virus in guinea pig embryonic tissue (GPEC) and human embryonic lung cells, and V-Oka live vaccine is prepared for preventing varicella. It was described in U.S. Pat. No. 4,000,256 that VZV was passaged 10-80 times in human embryonic fibroblasts WI-38 strain to produce live attenuated VZV vaccine. So far, only the "live attenuated varicella virus Oka strain" obtained by passage of the P-Oka strain in cells (special bulletin, No. 53-41202 Kimiaki), Lancet 2: 1288-1290, 1974) was approved by WHO for preparation vaccine for the prevention of varicella or herpes zoster, and the vaccine prepared from this strain has been widely used around the world [Requirement for Varicella Vaccine (Live) Adopted 1984: WHO Technical Report Series, No. 725, pp. 102-104, 1985]. Although population vaccinated with varicella vaccine have been reported to have a lower incidence of herpes zoster than populations of nature infection and most children are immonocompromised, the fact is that herpes zoster still appeared in vaccinated populations, and the V-Oka strain was also isolated from vesicles fluids of herpes zoster in vaccinated populations (Schmid D. S, et al. Impact of varicella vaccine on varicella-zoster virus dynamics, clinical microbiology reviews, January 2010, p 202-217).

The patent CN1163604C relates to the identification of the attenuated varicella vaccine Oka strain, which revealed at molecular level that the V-Oka strain is a mixed strains, which were composed of a number of different sequences. Wild strain may exists in the attenuated varicella virus strains, since it has been reported that patients inoculated with the V-Oka vaccine have developed herpes zoster containing the V-Oka strain. This means that there are still some potentially harmness in attenuated virus strains. However, so far there is no other vaccine against VZV on the market. This virus has strict species specificity, and human is the only natural host. And no animal models are available to be used in the research of the gene function of VZV. Furthermore, the virus has strong binding affinity with host cells. Free virus is easily to be inactivated. Therefore, it is very difficult to obtain VZV virus DNA that can be used for transformation. As a result, the research process of the gene function of this virus advances very slowly over a long time period.

With the application of a bacterial artificial chromosome (BAC) technology in the research, the advances of tissue culture technology and the breakthrough of barrier of organ transplant between heterogeneous organisms (the development of the combined immunodeficient mouse model), the study space of the gene function of species-specific VZV have been broaden. The study of gene functions of VZV can be carried out in vitro or it may be studied after transplanting into animals. In 2004, Kazuhiro N. et al. revealed in "Cloning of the varicella-zoster virus genome as an infectious bacterial artificial chromosome in *Escherichia coli*" that the whole genome of VZV Oka strain cloned into a BAC vector may proliferate in *Escherichia coli* and human embryonic lung cell. The BAC may be accurately excised by the enzyme Cre that is co-transformed into human embryonic lung cells. The resulted recombinant VZV virus has the same structure and characteristics as the parental virus P-Oka strain. The application of BAC has greatly facilitated the study of the gene function of VZV. It is possible to study each functional gene and thereby accelerate the research process of gene function of VZV.

The ORF7 of VZV, located at positions 8607-9386 of the viral genome, encodes a 29 kDa protein, which might locates within tegument. However, its function remains unknown.

The inventor, after extensive research, surprisingly found that ORF7 determines the function of the skin and sensory ganglion in patients infected with VZV. The ORF7 loses function when the any one of the followings occurs in ORF7: the whole or partial deletion, stop condon insertion, substituted by one or two bases, especially ORF7 deletion or flip reverse frameshift mutation. That is, VZV no longer infects human skin and sensory ganglion. So there is no potential risk of developing varicella or the risk of reactivation that causes herpes zoster (We define it here as ORF7 non-function caused by ORF7 deficiency, which function means contacting human skin and sensory ganglion). The ORF7-deletion VZV stain (VZV-7D BAC or VZV-7DRM BAC) may be further screened in *E. Coli* by antibiotics or galactose, in order to obtain the single clone strain. So there is no potential hazard of mixed V-Oka strains. It opens a door for developing a safer and more efficacious vaccine with ORF7 deleted or mutant virus.

SUMMARY OF THE INVENTION

In one aspect, the present invention relates to varicella virus (for example the P-Oka strain) with whole or partial ORF7 deletion, stop condon insertion, or with one or two bases substitution or insertion; and the described VZV cannot infect human skin and sensory ganglion.

The sequence of ORF7 (8607-9386 bp) is set forth below:

(SEQ ID NO: 1)
ATGCAGACGGTGTGTGCCAGCTTATGTGGATATGCTCGAATACCAACTGA

AGAGCCATCTTATGAAGAGGTGCGTGTAAACACGCACCCCCAAGGAGCCG

CCCTGCTCCGCCTCCAAGAGGCTTTAACCGCTGTGAATGGATTATTGCCT

GCACCTCTAACGTTAGAAGACGTAGTCGCTTCTGCAGATAATACCCGTCG

TTTGGTCCGCGCCCAGGCTTTGGCGCGAACTTACGCTGCATGTTCTCGTA

ACATTGAATGTTTAAAACAGCACCATTTTACTGAAGATAACCCCGGTCTT

AACGCCGTGGTCCGTTCACACATGGAAAACTCAAAACGGCTTGCTGATAT

GTGTTTAGCTGCAATTACCCATTTGTATTTATCGGTTGGCGCGGTGGATG

TTACTACGGATGATATTGTCGATCAAACCCTGAGAATGACCGCTGAAAGT

GAAGTGGTCATGTCTGATGTTGTTCTTTTGGAGAAAACTCTTGGGGTCGT

TGCTAAACCTCAGGCATCGTTTGATGTTTCCCACAACCATGAATTATCTA

TAGCTAAAGGGGAAAATGTGGGTTTAAAAACATCACCTATTAAATCGGAG

GCGACACAATTATCTGAAATTAAACCCCCACTTATAGAAGTATCGGATAA

TAACACATCTAACCTAACAAAAAAAACGTATCCGACAGAAACTCTTCAGC

CCGTGTTGACCCCAAAACAGACGCAAGATGTACAACGCACAACCCCCGCG

ATCAAGAAATCCCATGTTATGCTTGTATAA

In one embodiment of the invention, the whole or partial ORF7 is replaced by antibiotic resistance gene and/or non-functional nucleic acids sequence. Said non-functional nucleic acids sequence means it does not restore ORF7 function. That is, the VZV virus described above is still unable to infect skin and sensory ganglia. The non-functional nucleic acids sequence may encode no fusion protein, or it may encode fusion protein, provided that the encoded protein cannot restore ORF7 function. In one embodiment of the invention, the non-functional nucleic acids sequence described above is ORF7 with flip reverse frameshift mutation.

The term "ORF7 fragment" refers to the whole or partial ORF7 nucleic acids sequence.

In one embodiment of the invention, the described ORF7 fragment with flip reverse frameshift mutation is given in SEQ ID NO: 13.

In one embodiment of the invention, the antibiotic resistance genes are selected from *penicillium*, streptomycin and kanamycin resistance genes.

In one embodiment of the invention, the inventor generated recombinant clone based on the P-Oka clinically isolated strain from Dr. Ann Arvin's laboratory of the Stanford University School of Medicine, and the framework of the VZV-BAC (P-Oka), by applying the principle of homologous recombination. The full-length ORF7 has been replaced by kanamycin resistance gene to generate VZV-7D BAC, or by ORF7 fragments with flip reverse frameshift mutation to generate VZV-7DRM BAC. The sequence of said Kan$^r$ is given bellow:

(SEQ ID NO: 2)
ATGAGCCATATTCAACGGGAAACGTCTTGCTCGAGGCCGCGATTAAATTC

CAACATGGATGCTGATTTATATGGGTATAAATGGGCTCGCGATAATGTCG

GGCAATCAGGTGCGACAATCTATCGATTGTATGGGAAGCCCGATGCGCCA

GAGTTGTTTCTGAAACATGGCAAAGGTAGCGTTGCCAATGATGTTACAGA

TGAGATGGTCAGACTAAACTGGCTGACGGAATTTATGCCTCTTCCGACCA

TCAAGCATTTTATCCGTACTCCTGATGATGCGTGGTTACTCACCACTGCG

ATCCCCGGAAAAACAGCATTCCAGGTATTAGAAGAATATCCTGATTCAGG

TGAAAATATTGTTGATGCGCTGGCAGTGTTCCTGCGCCGGTTGCATTCGA

TTCCTGTTTGTAATTGTCCTTTTAACAGCGATCGCGTATTTCGTCTCGCT

CAGGCGCAATCACGAATGAATAACGGTTTTGTTGATGCGAGTGATTTTGA

TGACGAGCATAATGGCTGGCCTGTTGAACAAGTCTGGAAAGAAATGCATA

AACTTTTGCCATTCTCACCGGATTCAGTCGTCACTCATGGTGATTTCTCA

CTTGATAACCTTATTTTTGACGAGGGGAAATTAATAGGTTGTATTGATGT

TGGACGAGTCGGAATCGCAGACCGATACCAGGATCTTGCCATCCTATGGA

ACTGCCTCGGTGAGTTTTCTCCTTCATTACAGAAACGGCTTTTTCAAAAA

TATGGTATTGATAATCCTGATATGAATAAATTGCAGTTTCATTTGATGCT

CGATGAGTTTTCTAA

In particular, the invention provides a varicella zoster virus strain, which was deposited in China General Microbiological Culture Collection Center on Jul. 28,2009, its deposit number is CGMCC No.3207, and it was deposited at the China General Microbiological Culture Collection Center, Institute of Microbiology Chinese Academy of Sciences, NO.1 West Beichen Road, Chaoyang District, Beijing 100101, China.

The in vitro and in vivo studies confirmed that this virus strain does not infect human skin and sensory ganglion. So it is very possible that there is no potential risk of causing varicella or the risk of reactivation that causes herpes zoster. The virus grows in MRC-5 cell, MeWo cell and ARPE cell with the same growing characteristics with the P-Oka stain. Meanwhile, the growing and proliferation characteristics in thymus tissue culture are not changed. The strain retains all the glycoproteins of the P-Oka strain, so the immunogenicity should be the same as P-Oka strain. The strain is a single clone of the virus screened by kanamycin or galactose. Therefore, there is no potential risk of mixed clones of V-Oka strains. Due to the whole ORF7 deletion (VZV-7D BAC) or ORF7 flip reverse frameshift mutation (VZV-7DRM BAC), reverse mutation cannot be introduced to the strain of the invention. The live attenuated vaccine strain prepared from VZV-7D BAC or VZV-7DRM BAC is safer and more effective.

In another aspect, the invention relates to a method of preparation of varicella virus as described herein above, the method comprising the steps of:

1) cloning the genome of the wild-type VZV into a bacterial artificial chromosome (BAC) vector to generate recombinant varicella virus VZV-BAC with the whole or partial ORF7 deletion, one or several bases substitution or insertion, wherein said recombinant varicella virus is not able to infect human skin and sensory ganglion;

2) isolating the DNA from the VZV obtained in 1), and co-transforming MRC-5 cells, MeWo cells or ARPE cells with the isolated DNA and the recombinant plasmid containing the enzyme Cre;

3) excising BAC from MRC-5 cells, MeWo cells or ARPE cells by the enzyme Cre.

In one embodiment of the invention, the wild-type VZV is P-Oka stain, and the ORF7 in step 1) is replaced by Kan$^r$, or OFR7 fragment with flip reverse frameshift mutation. In one specific embodiment of the invention, the OFR7 fragment with flip reverse frameshift mutation is shown as SEQ ID NO: 13.

In another aspect, the invention also relates to a composition comprising any varicella virus as described above.

In yet another aspect, the invention also relates to a vaccine for prevention of varicella and/or herpes zoster, which contains any varicella virus as described above and excipient or carrier acceptable in a vaccine.

As used in the present invention, the term "vaccine for the prevention of varicella or herpes zoster" refers to varicella vaccine, herpes zoster vaccine, and vaccine for the prevention of varicella and herpes zoster.

In another aspect, this invention also relates to use of any one of the above described varicella virus in preparation of varicella and/or herpes zoster vaccine.

In another aspect, this invention also relates to use of any one of the above described varicella virus in preparation of an expression vector.

This invention also relates to an expression vector, which is composed of BAC and the DNA of any one of the above described varicella virus that is inserted into the BAC. An expression vector comprises the DNA of any one of the above described varicella virus. At least 10 kb of foreign gene may be inserted into the above described expression vector without affecting the function of the vector. It can also express the foreign genes. In addition, the expression vector is safe as a result of the deletion of ORF7. The expression vector may also be used for luciferase gene labeling (Zhang et al. Journal of Virology, September, 2007, p 9024-9033), in order to monitor the function of VZV-7DRM in vitro and in vivo.

In another aspect, the invention also relates to a recombinant vector comprising the above-mentioned expression vector and inserted foreign gene.

In another aspect, the invention also relates to a recombinant cell which contains the above-described expression vector or recombinant vector.

In one embodiment of the present invention, the host cells used as recombinant cell is selected from MRC-5, Mewo, ARPE, 2BS, WI-38, and KMB17 cell.

In another aspect, the invention also relates to a method for prevention of varicella and/or herpes zoster, comprising vaccinating a patient in need thereof with an effective amount of the above mentioned vaccine.

In this invention, the term "DPI" stands for "days post infection", which refers to the days after infection.

BRIEF DESCRIPTION OF THE DRAWINGS

FIG. 9A: MeWo cells and neuroblastoma (SH-SY5Y) cells transfected with DNA from WT, VZV-7DRM and VZV-7R. VZV-7DRM cannot grow in neuroblastoma cells.
FIG. 9B: dorsal root ganglion (DRG) isolated from the spinal cord of human embryos.
FIG. 9C: DRG was transplanted into the renal capsule of severe combined immunodeficiency mouse model (SCID-hu) and then infected by WT or VZV-7DRM. The virus growth is measured by IVIS instrument. VZV-7DRM cannot grow in severe combined immunodeficiency mouse transplanted with human tissues (SCID-hu).
FIG. 9D: After infection, increase of GFP intensity showed that WT VZV can grow in the DRG cultures.

DETAILED DESCRIPTION OF THE INVENTION

The embodiments of the invention will be described in details by referring to the following examples. One skilled in the art will recognize that these examples are intend to illustrate the implementation of the present invention, but not to limited the scope of the present invention. For those techniques or conditions not specifically illustrated, the procedures are carried out in accordance with the technology and conditions described in the art (for example, J. Sambrook, et al., "Molecular Cloning: A Laboratory Manual", third edition, Science Press; translated by Peitang Huang) or in accordance with the manufacture's instruction. Reagents or equipment are commercially available, unless otherwise specified.

Example 1. Construction of p-Oka BAC (VZV BAC)

(1) A BAC vector: A BAC vector, pUSF-6, contains the prokaryotic replication origin (ori), the replication and partition gene (repE, parA, and parB), the $Cam^r$ gene, a green fluorescent protein (gfp) gene, two 500-bp VZV fragments a and b (gray), and two loxP sites (white). pUSF-6 was digested with BamHI, resulting in a linear fragment; and was inserted in a VZV-containing cosmid, pvSpe23, by homologous recombination.

(2) Schematic diagram of the pOka genome shows that VZV contains a 125-kb nucleotide sequences with unique long (UL) and unique short (US) segments. The whole genome was digested into four VZV segments with overlapping region, and cloned into cosmid, resulting in four recombinant clones, namely pvFsp73, pvSpe14, pvPme19 and pvSpe23. pUSF-6 was inserted between ORF60 and ORF61 in a VZV cosmid, pvSpe23, by homologous recombination.

(3) The pvSpe23 containing a BAC vector (pUSF-6) was cotransfected with three other VZV cosmids into MeWo cells, and the resulting recombinant virus (VZVBAC) was able to replicate in MeWo cells and produced a green fluorescent plaque.

Figure 1:
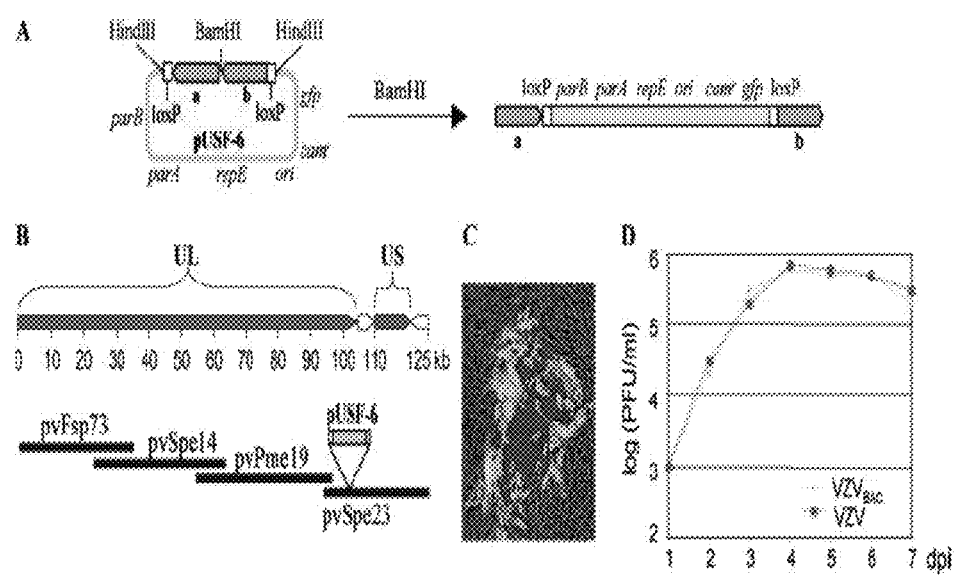
FIG. 1: Construction of P-Oka BAC (VZV BAC) vector.
Figure 2:
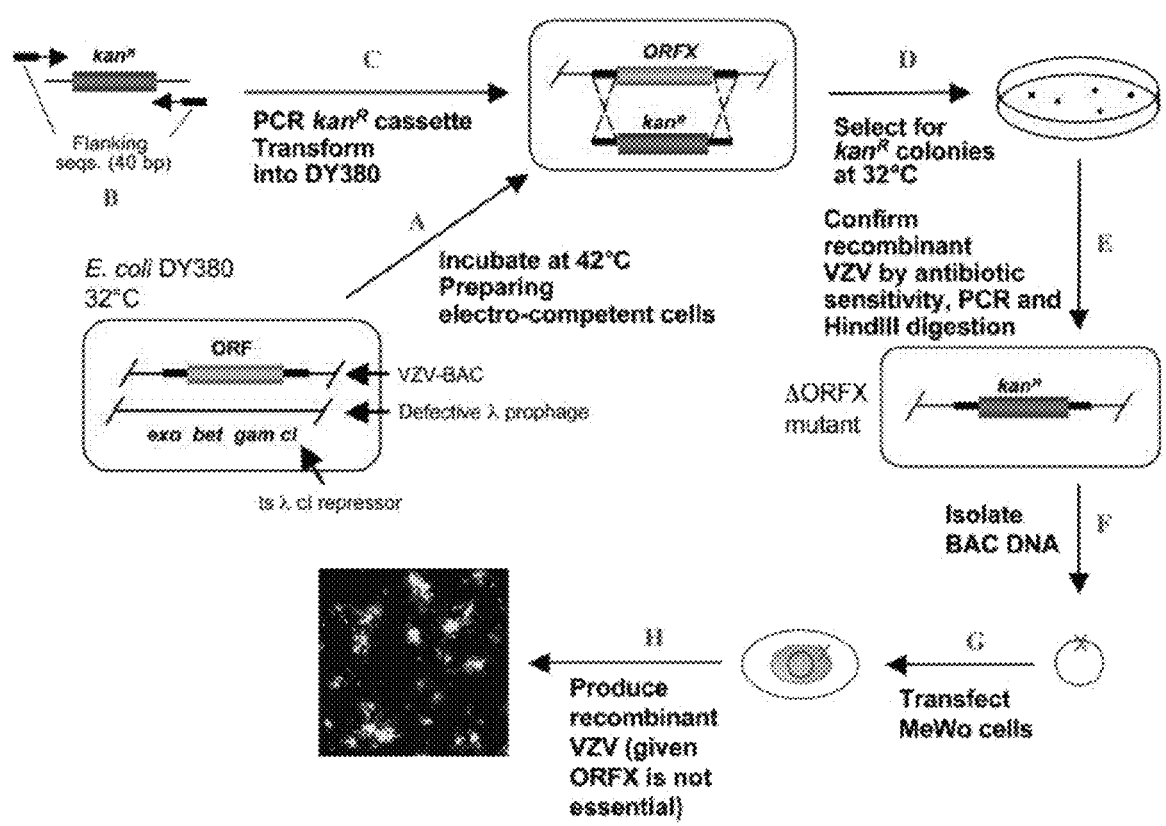
FIG. 2: Preparation of ORF7 deleted VZV BAC strain (VZV-7D BAC).
Figure 3:
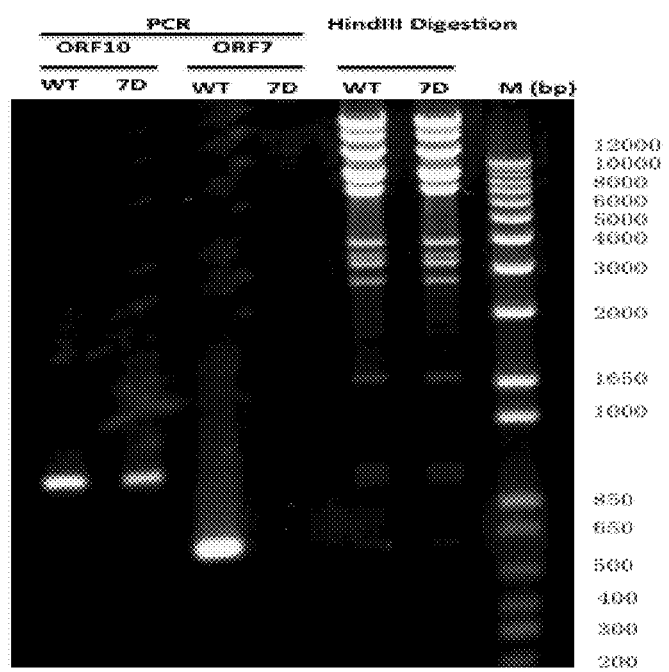
FIG. 3: Electrophoresis of ORF7 deleted VZV.
Figure 4A:
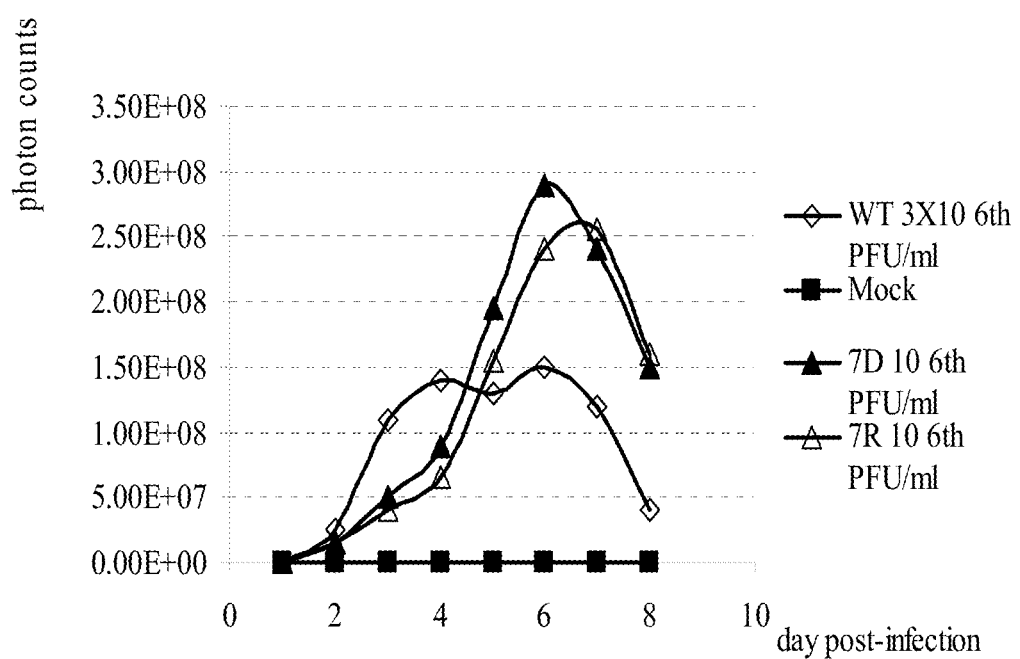
FIG. 4A: Culture of VZV-7D in dorsal root ganglion the growth curve of wild type virus (WT), reverse mutant virus (7R), deficient virus (7D) cultured in MeMo cell.
Figure 4B:
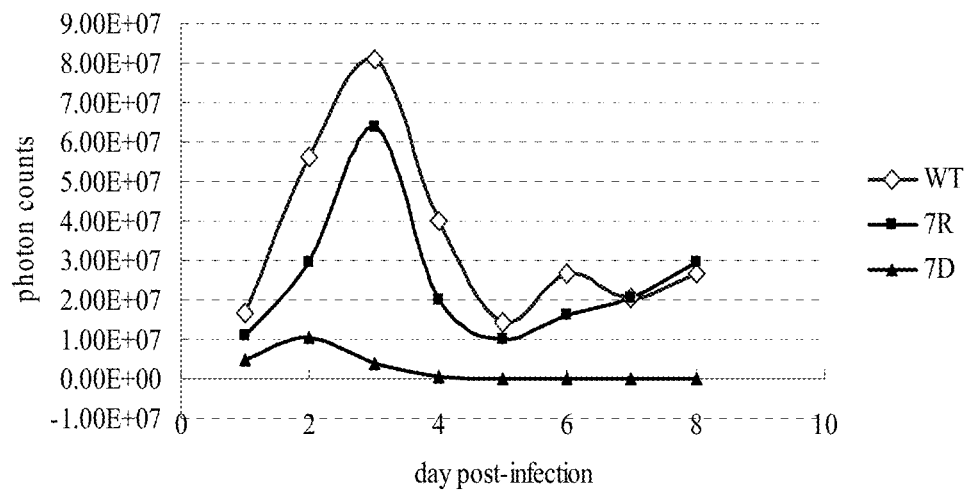
FIG. 4B: Culture of VZV-7D in dorsal root ganglion the growth curve of wild type virus (WT), reverse mutant virus (7R), deficient virus (7D) cultured in the dorsal root ganglion (DRG).
Figure 5:
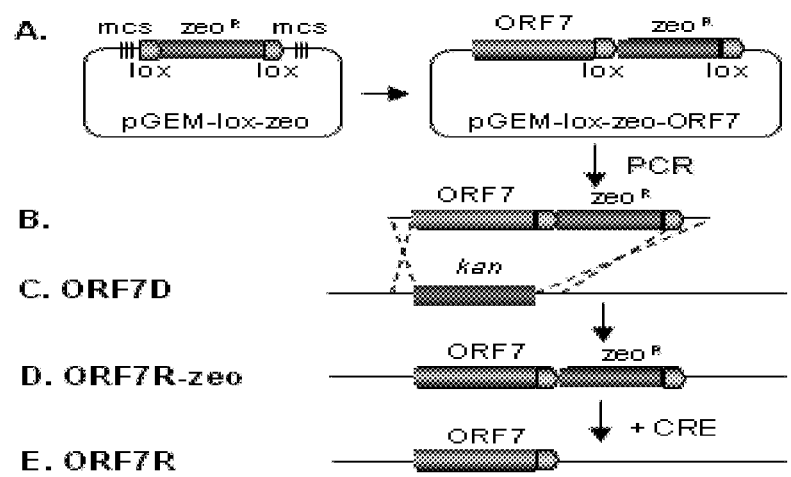
FIG. 5: Preparation of ORF-7 reverse mutant VZV (VZV-7R).

The procedures is also shown in FIG. 1.

The growth curve of VZV BAC was compared to that of wild-type pOka. Plaque forming unit (PFU) at each dpi was recorded. The results indicates that VZV BAC (green) has no detectable growth defect, which is consistent with in vitro grown of the parental virus.

Example 2. Generation and Validation of ORF7 Deficient VZV BAC (VZV-7D BAC)

ORF7 deleted mutant was constructed by referring to previously described luc VZV BAC (Zhang et al. Journal of Virology, September, 2007, p 9024-9033). The procedures were described in FIG. 2 and below.

(1) Two primers were designed to contain 20-bp of homologous nucleotides of the kanamycin resistance gene and 40-bp of homologous nucleotides of the flanking sequences adjacent to either the start or stop codon of the ORF7 being targeted for deletion. The sequences of primer F1 and R1 are given below:

```
F1:
                                   (SEQ ID NO: 3)
GAT TTA TCC ATA GTT CAA TAC GTT GGA AAG CCA GTC

AAT CGC TCT TGT TGG CTA GTG CGT A;

R1:
                                   (SEQ ID NO: 4)
AAA CAT ACA CCA GAA ACG TTT TTA GTT TTT ATT TCA

ATA TTC TGC CAG TGT TAC AAC CAA.
```

The $Kan^R$ gene was amplified from the plasmid pGEM-oriV/kan1 (Netterwald, Yang et al. 2005). The PCR products were digested with DpnI and recovered by a gel extraction kit (Qiagen).

(2) About 200 ng of each PCR product was transformed into DY380 strain carrying the VZVLuc BAC via electroporation at 1.6 kV and 250 uF using BioRad Gene Pulser II equipment.

(3) The DY380 strain serving as a highly efficient homologous recombination system allows recombination of homologous sequences as short as 40 bp. The homologous recombination between kanamycin resistance gene ($kan^r$) and ORF7 is realized by the recombinant enzyme, which is activated at 42° C. and suppressed at 32° C. As a result, ORF7 was replaced by $Kan^r$. The single recombinants were selected on agar plates containing 30 μg/ml of kanamycin at 32° C. DNA of VZV mutant (ORF7 deletion) were isolated from *E. coli*.

(4) The virus genome's integrity was verified by HindIII digestion and the recombinant DNA was confirmed by PCR analysis. It is confirmed that ORF7 deficient BAC was obtained (VZV-7D BAC), with ORF7 replaced by $Kan^r$.

Example 3. Generation and Verification of VZV BAC with Flip Reverse Frameshift Mutation (VZV-7DRM BAC)

Strategy: The ORF7 of wild type virus was replaced by galk gene. The recombinant VZV with galk gene shall produce bright red plaques on MacConkey agar with galactose as the only carbon source. The single clone would be chosen by this method. Then replace the galk gene with flip reverse frameshift mutation sequences and select single clone on complete and minimal media plates to obtain VZV-7DRM BAC.

Detailed protocol is given below:

(1) Design amplification primers F2 and R2 to amplify galk gene from pgalk (1-82 bp: promoter; 83-1231 bp: galK open reading frame). The forward and reverse primers each have at 5' 60 bp homology sequences flanking ORF7. Galk sequence is given below (SEQ ID NO:5):

```
                                   (SEQ ID NO: 5)
CCTGTTGACAATTAATCATCGGCATAGTATATCGGCATAGTATAATACGA

CAAGGTGAGGAACTAAACCCAGGAGGCAGATCATGAGTCTGAAAGAAAAA

ACACAATCTCTGTTTGCCAACGCATTTGGCTACCCTGCCACTCACACCAT

TCAGGCGCCTGGCCGCGTGAATTTGATTGGTGAACACACCGACTACAACG

ACGGTTTCGTTCTGCCCTGCGCGATTGATTATCAAACCGTGATCAGTTGT

GCACCACGCGATGACCGTAAAGTTCGCGTGATGGCAGCCGATTATGAAAA

TCAGCTCGACGAGTTTTCCCTCGATGCGCCCATTGTCGCACATGAAAACT

ATCAATGGGCTAACTACGTTCGTGGCGTGGTGAAACATCTGCAACTGCGT

AACAACAGCTTCGGCGGCGTGGACATGGTGATCAGCGGCAATGTGCCGCA

GGGTGCCGGGTTAAGTTCTTCCGCTTCACTGGAAGTCGCGGTCGGAACCG

TATTGCAGCAGCTTTATCATCTGCCGCTGGACGGCGCACAAATCGCGCTT

AACGGTCAGGAAGCAGAAAACCAGTTTGTAGGCTGTAACTGCGGGATCAT

GGATCAGCTAATTTCCGCGCTCGGCAAGAAAGATCATGCCTTGCTGATCG

ATTGCCGCTCACTGGGGACCAAAGCAGTTTCCATGCCCAAAGGTGTGGCT

GTCGTCATCATCAACAGTAACTTCAAACGTACCCTGGTTGGCAGCGAATA

CAACACCCGTCGTGAACAGTGCGAAACCGGTGCGCGTTTCTTCCAGCAGC

CAGCCCTGCGTGATGTCACCATTGAAGAGTTCAACGCTGTTGCGCATGAA

CTGGACCCGATCGTGGCAAAACGCGTGCGTCATATACTGACTGAAAACGC

CCGCACCGTTGAAGCTGCCAGCGCGCTGGAGCAAGGCGACCTGAAACGTA

TGGGCGAGTTGATGGCGGAGTCTCATGCCTCTATGCGCGATGATTTCGAA

ATCACCGTGCCGCAAATTGACACTCTGGTAGAAATCGTCAAAGCTGTGAT

TGGCGACAAAGGTGGCGTACGCATGACCGGCGGCGGATTTGGCGGCTGTA

TCGTCGCGCTGATCCCGGAAGAGCTGGTGCCTGCCGTACAGCAAGCTGTC

GCTGAACAATATGAAGCAAAAACAGGTATTAAAGAGACTTTTTACGTTTG

TAAACCATCACAAGGAGCAGGACAGTGCTGA
```

The sequences of Primer F2 and R2 are given below:

```
F2
                                   (SEQ ID NO: 6)
ACCGAATCGTCGGTTTGGAGGATTTATCCATAGTTCAATACGTTGGAAAG

CCAGTCAATCATGCCTGTTGACAATTAATCATCGGCA

R2
                                   (SEQ ID NO: 7)
TAATTTTATATACAAAATAAAAACATACACCAGAAACGTTTTTAGTTTTT

ATTTCAATATTCAGCACTGTCCTGCTCCTT
```

(2). Use those primers to amplify the galk cassette. Digesting the product with DpnI overnight and purify it;

(3). Transform the VZV BAC into SW102 strain of *E. coli;*

(4). Inoculate a single colony onto 5 ml of LB-CM (LB with chloramphenicol) and grow overnight at 32° C.;

(5). Inoculate the overnight culture into 250 ml of LB-CMol and grow at 32° C. with shaking till an O.D. of 0.4-0.6;

(6). Prepare the electrocompetent cells (SW102 transformed with VZV BAC);

(7). Transform the electrocompetent cells (SW102 transformed with VZV BAC) prepared in step (6) with 1-2 μl (~200 ng) of the purified PCR product from step (2), with the electroporation parameters described in example 2.

(8). Recover the transformants for one hour in 1 ml of LB at 32° C.

(9). After the recovery period, wash the bacteria 3× in 1×M9 salts as follows: centrifuge the culture at 13,200 RPM for 15 sec, and remove the supernatant with a pipette. Resuspend the pellet in 1×M9 salts, and centrifuge it again as above. Repeat the washing step once more. After three washes, remove the supernatant and resuspend the pellet in 1 ml of 1×M9 salts. Then plate the suspension of the pellet, 10× serial dilutions and 100× serial dilutions onto M63 minimal media plates with galactose, leucine, biotin, and chloramphenicol;

(10). Incubate the plates for 3 days at 32° C.;

(11). Streak a few colonies onto MacConkey agar with galactose+chloramphenicol plates to obtain single colonies. The colonies appearing after 3 days of incubation should be Gal+, but in order to get rid of any Gal− contaminants, it is important to obtain single, bright red colonies before proceeding to the next step.

(12). Pick a single, bright red (Gal+) colony and inoculate into a 5 ml LB-CM medium and culture overnight 32° C.; Prepare the BAC DNA from the overnight culture and verify the galk gene by PCR; the primers used are:

```
F3:
                                           (SEQ ID NO: 8)
CCTGTTGACAATTAATCATCGGCA

R3:
                                           (SEQ ID NO: 9)
TCAGCACTGTCCTGCTCCTT
```

(13). Using primers F4 (SEQ ID NO: 10) and R4 (SEQ ID NO:11) to amplify the 457 bp sequence adjacent to 3' of ORF7 stop codon (the sequence of 457 bp ORF is set forth in SEQ ID NO:12). Since the primers F4 and R4 are designed to introduce 1 base's frameshift, the PCR product are produced with frameshift mutation.

The sequences of F4 and R4 are given below:

```
F4
                                          (SEQ ID NO: 10)
CGAATCGTCGGTTTGGAGGATTTATCCATAGTTCAATACGTTGGAAAGCC

AGTCAATTTAATGGGATTTCTTGATCGCGGGG

R4:
                                          (SEQ ID NO: 11)
AATTTTATATACAAAATAAAAACATACACCAGAAACGTTTTTAGTTTTTA

TTTCAATATGTGGTCCGTTCACACATGGAAAAC
```

457 bp open read frame:

```
                                          (SEQ ID NO: 12)
CAGACGGTGTGTGCCAGCTTATGTGGATATGCTCGAATACCAACTGAAGA

GCCATCTTATGAAGAGGTGCGTGTAAACACGCACCCCCAAGGAGCCGCCC

TGCTCCGCCTCCAAGAGGCTTTAACCGCTGTGAATGGATTATTGCCTGCA

CCTCTAACGTTAGAAGACGTAGTCGCTTCTGCAGATAATACCCGTCGTTT

GGTCCGCGCCCAGGCTTTGGCGCGAACTTACGCTGCATGTTCTCGTAACA

TTGAATGTTTAAAACAGCACCATTTTACTGAAGATAACCCCGGTCTTAAC

GCCGTGGTCCGTTCACACATGGAAAACTCAAAACGGCTTGCTGATATGTG

TTTAGCTGCAATTACCCATTTGTATTTATCGGTTGGCGCGGTGGATGTTA

CT.
```

Repeat steps 4 through 10 above to obtain electrocompetent SW102 cells.

(14). Transform 50 μl of heat-shocked bacteria of step (13) with 200 ng PCR product with homology to the area flanking the galK gene of step (2). Recover in 10 ml LB in a 50 ml baffled conical flask by incubating with shaking in a 32° C. waterbath for 4.5 hours. This long recovery period serves to obtain recombined VZV BAC that only contains the sequences of interest (and thus remove VZV BAC containing the galK cassette). As primer F4 is composed of 60 bp homologous sequence flanking the 5' of the ORF7 and 457 bp reverse sequences adjacent to 3' of ORF7, and primer R4 is composed of 60 bp homologous sequence flanking 3' of the ORF7 and 457 bp forward sequence adjacent to 3' of ORF7, homologus recombination between the amplified PCR product and galk gene in ORF7 locus leads to flip reverse link of 3' 457 bp, resulting in flip reverse frameshift mutation (SEQ ID NO:13), without expressing function. The flip reverse framshift mutation sequence is given below:

(SEQ ID NO: 13)
CATGGGATTTCTTGATCGCGGGGGTTGTGCGTTGTACATCTTGCGTCTGT
TTTGGGGTCAACACGGGCTGAAGAGTTTCTGTCGGATACGTTTTTTTTGT
TAGGTTAGATGTGTTATTATCCGATACTTCTATAAGTGGGGGTTTAATTT
CAGATAATTGTGTCGCCTCCGATTTAATAGGTGATGTTTTTAAACCCACA
TTTTCCCCTTTAGCTATAGATAATTCATGGTTGTGGGAAACATCAAACGA
TGCCTGAGGTTTAGCAACGACCCCAAGAGTTTTCTCCAAAAGAACAACAT
CAGACATGACCACTTCACTTTCAGCGGTCATTCTCAGGGTTTGATCGACA
ATATCATCCGTAGTAACATCCACCGCGCCAACCGATAAATACAAATGGGT
AATTGCAGCTAAACACATATCAGCAAGCCGTTTTGAGTTTTCCATGTGTG
AACGGAC;

(15). As in step 9, spin 1 ml culture and wash 3× in 1×M9 salts, and resuspend in 1 ml 1×M9 salts. Plate the suspension of the pellet and 10×dilution (each 1041) on M63 minimal media plates with glycerol, leucine, biotin, 2-deoxy-galactose, and chloramphenicol;

(16), Incubate at 32° C. for three to four days;

(17). Pick colonies and streak them onto an LB-CM plate and a Galk-M63 CM minimal media plate. Select single colonies that grow on the LB-CM but not on the minimal media plate. Extract virus DNA and verity integrity by HindIII digestion and confirm recombinant DNA by PCR. It is confirmed that VZV BAC with ORF7 flip reverse framshift mutation (VZV-7DRM BAC).

The reagents used in the above procedures are prepared as in Table 1:

TABLE 1

| the reagents used in this example and there formulation | |
|---|---|
| Reagents | formulation |
| M63 galactose minimal plates (1 L) | Autoclave 15 g agar in 800 mL $dH_2O$<br>After slight cooling, add 200 mL autoclaved 5X M63 medium and 1 mL 1M $MgSO_4 \cdot 7H_2O$;<br>Let cool to 50° C. Add 10 mL of 20% galactose, 5 mL fresh biotin, 4.5 mL leucine, and 1 mL 1000X chloramphenicol<br>Mix the medium with magnetic stirrer, then pour plates |
| 5X M63 medium | 10 g $(NH_4)_2SO_4$<br>68 g $KH_2PO_4$<br>2.5 mg $FeSO_4 \cdot 7H_2O$<br>to 1 L with $dH_2O$<br>adjust to pH 7.0 with KOH<br>autoclave |
| 1M $MgSO_4 \cdot 7H_2O$ | 24.65 g $MgSO_4 \cdot 7H_2O$ dissolved in 100 mL $dH_2O$ autoclave |
| 20% galactose | 20 g galactose dissolved in 100 mL $dH_2O$ autoclave |
| 0.2 mg/mL d-biotin | 20 mg d-biotin dissolved in 100 mL $dH_2O$ then sterilization by filtering |
| 10 mg/mL L-leucine | 1.0 g L-leucine dissolved in 100 mL $dH_2O$ by heating, then sterilization by filtering. |

Example 4. Generation of VZV-7D and VZV-7DRM Viruses (1). Extract DNA from the VZV 7D BAC obtained in Example 2;

(2). The purified DNA was separately transfected into MRC-5 cell (Marchini, Liu et al., 2001) via electroporation (the proliferation of the virus can be monitored by GFP carried on BAC); or, the purified DNA was co-transfected with a Cre expression vector into MRC-5 cell (Marchini, Liu et al., 2001). The BAC is accurately excised at loxP sites flanking BAC by Cre, and VZV 7D virus was obtained.

Similarly, VZV-7DRM virus with ORF7 flip reverse framshift mutation was also obtained. Since the VZV7DRM contains only partial ORF7 which is the flip reverse sequences, it cannot be expressed and have no ORF7 function. Both VZV-7DRM and VZV-7D have the same function.

Example 5. Verification of VZV 7D

The monolayer MRC-5 cells were infected with VZV-7D prepared in Example 4 and cultured in MEM medium supplemented with 2% bovine serum. When nearly 80% of the cells exhibit cytopathic effect, discard the culture medium, harvest the cells and extract DNA. P-Oka serves as control. ORF-10 and ORF-7 genes were amplified by PCR. DNA of VZV-7D and P-Oka was digested by HindIII. PCR products and HindIII digestion products were subjected to electrophoreses in 0.5% agarose gel. The result was shown in FIG. 3. PCR products of ORF-10 in VZV-7D is the same as in P-Oka, but ORF-7 band in VZV-7D is absent. This confirmed that ORF-7 in VZV-7D has been deleted. The difference of the profiles of virus DNA digested by HindIII between VZV-7D and P-Oka is not visible.

Example 6. Culture of VZV-7D in Human Dorsal Root Ganglia

Cervical and thoracic Dorsal Root Ganglia (DRG) were isolated from human fetal spine (20-week-gestational). The DRG were washed briefly in ice-cold 1×PBS with 1% Penicillin/Streptomycin and then transferred to ice-cold tissue culture medium (DEM with 15% heat-inactivated bovine fetal serum and 1% Penicillin/Streptomycin). Each DRG was placed separate on a collagen coated coverslip in 6 well-plates, covered with 0.5 ml medium and cultured for 5 days with one change of medium. 50% MeWo cells were prepared in 6-well plates for titrating and for generation of growth curve (FIG. 4A). On the sixth day, Mewo cells freshly infected by P-Oka, VZV-7D and VZV-7R were harvested and resuspended in medium to a final volume of 1 ml. Each DRG grows separately on collagen coated coverslip in 6 well plates. 10 μl suspension was used for determining virus titers, 2 μl for generating growth curve of infected MeWo cells. The rest of the cell suspension was passed through a 27 gauge needle 20 times and the cell debris was pelleted by centrifugation at 4000 rpm for 10 minutes. The supernatant was divided into equal amounts and used to infect DRGs (~120 μl/sample); in addition, 2 drops (20 μl) of cell suspension were used to infect another set of DRG. After 3 hours incubation in 37° C./5% $CO_2$, the DRG were washed with 1×PBS and fresh media were added. Measurements of luciferase activity were taken at 24 h intervals. The samples were incubated with 150 μg/ml D-luciferin at 37° C. for 10 minutes. The photons were counted by IVIS instrument and analyzed by a software. The results were shown in FIG. 4B.

Results shown that VZV-7D grow well in MeWo cells, but it hardly grows in DRG. The fact that VZV-7D do not infect DRG provides a basis for developing safe attenuated live vaccine.

Example 7. Construction and Validation of VZV-7D Reverse Mutant (VZV-7R)

ORF7 deletion mutation can be identified not only by the HindIII digestion, but also by complete VZV virus obtained by homologous recombination. That is to say, the complete VZV is rescued by the mechanism of homologous recombination, see FIG. 5). ORF7 fragment was amplified by PCR using invitrogen high fidelity platinum Taq DNA polymerase kit and cloned into the plasmid pGEM-lox-zeo between the NotI and BglII sites to form pGEM-zeo-ORF7 plasmid. The cloned fragment was verified by sequencing analysis and it is shown that no incorrect condons were introduced into ORF7 by PCR amplification. Then the zeoR-ORF7 cassette was amplified by PCR from pGEM-zeo-ORF7 using two primers.

```
F5:
                                        (SEQ ID NO: 14)
GAT TTA TCC ATA GTT CAA TAC GTT GGA AAG CCA GTC

AAT CAT GCA GAC GGT GTG TGC CAG;

R5:
                                        (SEQ ID NO: 15)
AAA CAT ACA CCA GAA ACG TTT TTA GTT TTT ATT TCA

ATA TGG ATG GAT CCA TAA CTT CGT.
```

The resultant PCR product contains 40-bp homologous VZV segments at each end, said segments are adjacent to the $kan^R$ gene and are located in the deleted ORF7 gene. The resultant chimeric PCR product was transformed into DY380 strain carrying ORF7D BAC clones via electroporation as described above. The recombinants were selected on agar plates containing 50 μg/ml of zeocin (Invitrogen)

and 12.5 µg/ml chloramphenicol at 32° C. The correct VZV clones were confirmed by their antibiotic sensitivities. The correct clones should be resistant to chloramphenicol, hygromycin, zeocin, and sensitive to kanamycin and ampicillin. These clones were further validated by restriction digestion and PCR analysis.

The verified clones (*E. coli* DY380 with ORF7 deletion or rescuer luc VZV BAC) were inoculated in 500 ml LB with 12.5 µg/ml chloramphenicol at 32° C. for 20 hours. VZV-BAC DNAs were isolated using the Nucleobond Maxiprep BAC DNA isolation kit (BD Biosciences, Palo Alto, Calif.), and used to tranfect MRC-5 cells using the FuGene6 transfection reagent (Roche, Indianapolis, Ind.) according to the manufacturer's instruction. For each well (35-mm) of the 6-well plates, the ratio of DNA to transfection reagent was 1.5 µg:6 µl. VZV plaques were normally visible at 3 days post transfection. To remove the BAC vector (flanked by two loxP sites) from the VZV genome, a Cre expression vector was co-transfected with VZV BAC DNA into MRC-5 cells (Marchini, Liu et al. 2001). BAC was accurately deleted by Cre enzyme to produce the whole VZV.

ORF-7 rescue virus has the same growth and proliferation characteristics with that of the P-Oka strain. These result showed that the function of ORF-7 can be restored by reverse mutation.

Example 8. Culture of VZV-7DRM in Mewo Cells

Figure 6:
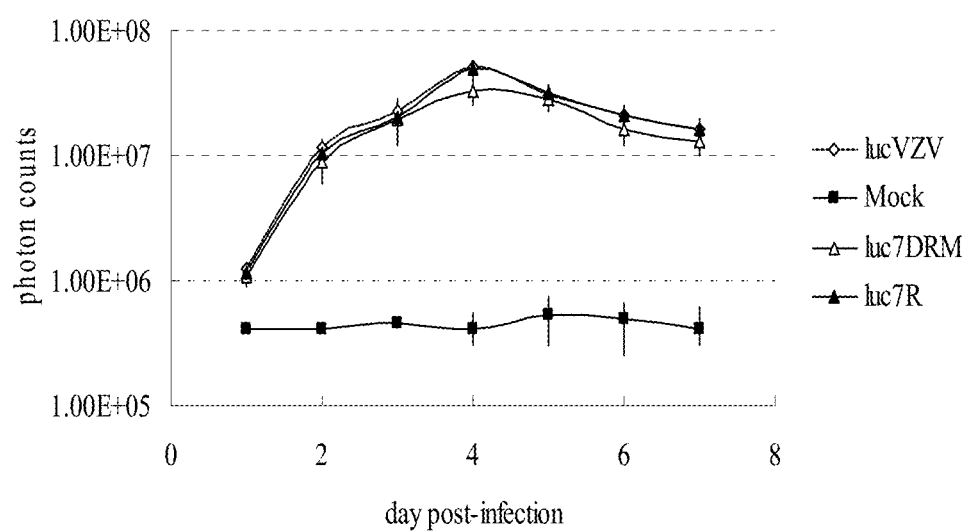
FIG. 6: the growth curve of VZV-7DRM with a fluorescent tag (luc) cultured in human MeWo cells.

The monolayer MeWo cells in 6-well plates were either mock infected or infected with lucVZV-7DRM (VZV-7DRM with Luc), luc7VZV-7R (VZ-7R with Luc) and lucVZV (P-Oka strain with Luc). Mewo cells were cultured in MEM medium with 2% bovine serum at 37° C. 24 hours post infection, D-luciferin was added to the cultured wells to a final concentration of 150 µg/ml. After 10 minutes incubation at 37° C., the luminescence in the different wells was recorded simultaneously using the IVIS Imaging System (50 Series, Xenogen Corporation, Alameda, Calif.) in triplicate. After measurement, the luciferin-containing media were replaced by regular cell culture media. This measurement was repeated every 24 hours for 7 days. The growth curves were generated by plotting the average data against time (FIG. 6).

Human MeWo cells were either mock infected or infected by wild type VZV (lucVZV) or VZV-7DRM or VZV-7D rescue strain (luc7R) and cultured for 7 days. The photon count were recorded by IVIS system every day post infection in triplicate. A growth curve was generated by plotting the average photon counts against time. An error bar was indicated in the figures. The results of this experiment showed that VZV-7DRM and VZV-7R grow as well as wild type virus in MeWo cells. Meanwhile, it was shown that VZV-7DRM is able to proliferate normally after insertion of BAC. The genes carried by BAC is also able to be expressed. That is, VZV-7DRM can be used as expression vector of heterogenous genes.

Example 9. Culture of VZV-7DRM in Human Thymus Tissues

Figure 7:
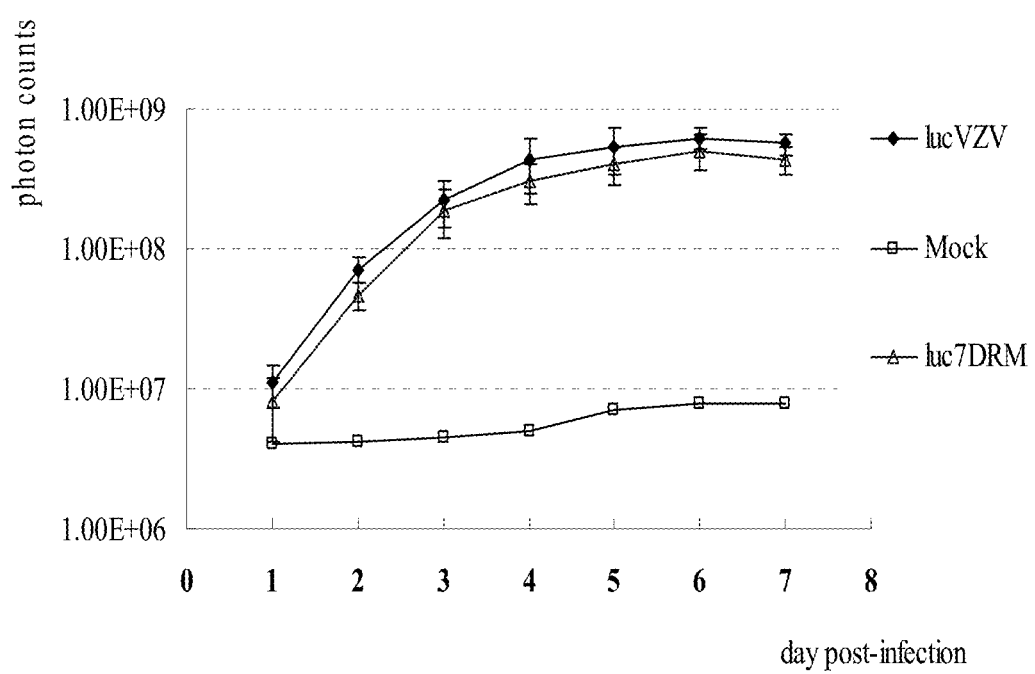
FIG. 7: the growth curve of VZV-7DRM with a fluorescent tag (luc) cultured in human thymus tissue culture (TOC).

Human thymus-liver tissue were co-transplanted as xenograft into male CB-17SCID/beige mice. The combined transplant of human thymus-live tissues are constructed according to methods described in the literature (Jennifer F. M., Journal of Virology, September 1995, p 5236-5242). 3 months post transplantation, the human thymus-live xenografts were exposed by surgery, and were either mock infected or infected with $2 \times 10^3 - 4 \times 10^3$ PFU of lucVZV-7DRM (VZV-7DRM with luciferase) and lucVZV (P-Oka with luciferase) cultured from 10-20 µl of MeWo cells in triplicate. Fluorescence intensity was measured each day post infection. 250 µl of substrates of luciferase, D-luciferin, was added by i.p. injection. After 10 minutes, the fluorescence in xenograft was recorded in triplicates using the IVIS Imaging System according to the methods described in Example 8. The results were shown in FIG. 7.

Cultured human thymus tissues were either mock infected or infected with wild type VZV, or VZV-7DRM for 7 days. Photon counts were measured using IVIS system each day post infection (DPI), and growth curves were generated by plotting average photon counts against time. Error bar from three data measurements are indicated in the figures. This experiment showed that VZV-7DRM mutant can grow in thymus tissues (T-cells) like wild type VZV.

Similar experiments demonstrated that VZV-7D can also grow in thymus tissues (T-cells) like wild type VZV.

Example 10. Culture of VZV-7DRM in Skin

Figure 8:
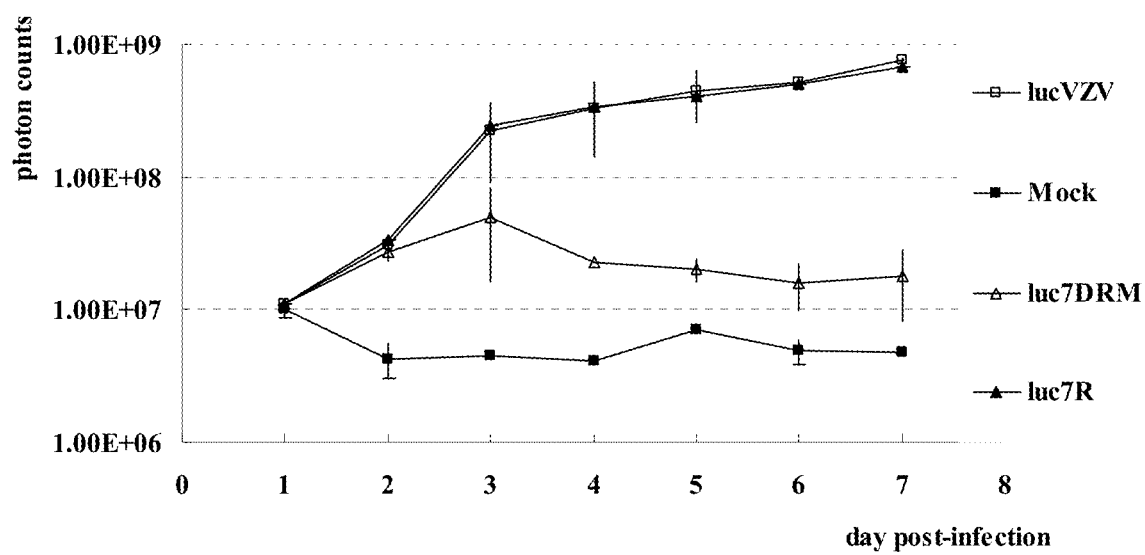
FIG. 8: the growth curve of VZV-7DRM with a fluorescent tag (luc) in human skin tissue culture (SOC).

Human fetal skin was transplanted into SCID mice subcutaneously as integral grafts in accordance with method described in literature (Jennifer F. M. Journal of Virology, September 1995, p 5236-5242). 4 week after transplantation, mice skin were either mock infected or infected with lucVZV-7DRM (VZV-7DRM with Luc), luc7VZV-7R (VZ-7R with Luc) and lucVZV (P-Oka strain with Luc) in triplicate. Fluorescence intensity was measured each day post infection. 250 µl of substrates of luciferase, D-luciferin, was added by i.p. injection. After 10 minutes, the fluorescence in xenograft was recorded in triplicates using the IVIS Imaging System according to the methods described in Example 8. The results were shown in FIG. 8.

Cultured human skin tissues were either mock infected or infected with wild type VZV (P-Oka strain) or ORF7 deficient mutant (VZV-7DRM) or ORF7 reverse mutate (VZV-7R) for 7 days. Photon counts were measured using IVIS system each day post infection (DPI), and growth curves were generated by plotting average photon counts against time. Error bar from three data measurements are indicated in the figures. This experiment showed that VZV-7DRM mutant has great growth defects in skins, which function defects can be restored by reverse mutation in VZV-7DRM Similar experiments find VZV-7D mutant also has great growth defects in skins, which function defects can be restored by reverse mutation in VZV-7D.

Example 11. Experiments Confirmed that ORF7 is Essential for VZV to Infect Nerve Cells 1. Neurocytoma Cell Infection MeWo cell and neurocytoma cell line SH-SY5Y were transfected with DNAs from wild type (WT), ORF7-deleted (VZV-7DRM) and ORF7-reverse mutant (VZV-7R) BAC. The results showed WT, VZV-7R can grow well in MeWo cell and neurocytoma cells; however, VZV-7DRM cannot grow in neurocytoma cells (FIG. 9A). This suggests that ORF7 is most likely essential for VZV's infection of nerve cell.

2. DRG Graft Infection

To further verify the results of test 1 in this example, human fetal DRGs were transplanted into SCID mice, and used as animal model of virus infection. The results showed that wild type virus becomes latent after a short replication cycle (a fluorescent phenomenon), while VZV-7D cannot replicate in DRG graft. These results showed that ORF7 is most likely a neurotropic factor of VZV (FIGS. 9B-D).

The above two tests demonstrated that ORF7 is essential for VZV's infection of neurons.

Example 12. Preparation of Vaccine and Immunogenicity Assay of VZV-7DRM

Monolayer ARPE cell or MRC-5 cells were infected with VZV-7DRM at a MOI of 0.1. After virus attaches to cells for 40 minutes, medium were added to the flasks, which were incubated at 35° C. The cells were harvested by digestion with 0.1% EDTA when about 80% of the cells presented cytopathy (generally 3 days). The harvest cells were centrifuged, and protection agents were added; after crashing and clarification, vaccines were obtained.

Guinea pigs (weighting about 250 g) were vaccine with reconstituted vaccine at 5 guinea pigs per vaccine, 5000 pfu/0.5 ml/dose. 4 weeks after first immunization, one boost immunization was given. P-Oka and V-Oka serves as control.

2 weeks after boost immunization, the blood was collected by cardiopuncture. The serum antibody titers were detected by gp-ELISA. The antibody neutralizing ability against virus were determined by immuno-inhibition assay. Ten-fold dilutions of serums before and after vaccination were mixed with virus at 1:1 ratio. After incubation at 37° C. for 60 minutes, the mixtures were used to infect MRC-5 cells. After incubation at 37° C. in 5% $CO_2$ for 7 days, the medium were removed and the cells were stained with coomassie blue. The virus titers are calculated through plaque forming unit counts. The degree of antibody neutralizing virus is calculated as 100×(virus titer neutralized by serum before vaccination–virus titer neutralized by serum after vaccination)/virus titer neutralized by serum before vaccination. The result is given in table 2.

TABLE 2

Antibody titer and antibody neutralization degree of guinea pig sera from varicella virus inoculation

| sera | antibody titer (GMT) | antibody neutralization degree (%) | | |
|---|---|---|---|---|
| | | P-Oka | V-Oka | VZV-7DRM |
| Anti-P-Oka | 246 | 39 | 74 | 26 |
| Anti-V-Oka | 279 | 47 | 84 | 68 |
| Anti-VZV-7DRM | 277 | 65 | 85 | 67 |

The result showed VZV-7DRM possesses good immunogenicity, whose antibody neutralization degree is comparable with that of V-Oka. Serum after VZV-7DRM vaccination has good neutralizing effect on all three kinds of virus, and shows potential for developing as vaccines.

Similar experiments showed that VZV-7D has also good immunogenicity and potential for developing as vaccines.

Example 13. Preparation of Biological Active Material Using VZV-7DRM as Vectors EV71-VP1 cassette was amplified from pT-VP1 plasmid by PCR with EV71-VP1 primers containing flanking homology to ORF7.

EV71-VP1 Cassette sequence is given below:

(SEQ ID NO: 16)
ATGGGAGATAGGGTAGCAGATGTAATTGAAAGCTCCATAGGAGATAGCGT

GAGCAGAGCCCTCACTCACGCTCTACCAGCACCCACAGGCCAGAACACAC

AGGTGAGCAGTCATCAACTGGATACAGGCAAGGTTCCAGCACTCCAAGCT

GCTGAAATTGGAGCATCATCAAATGCTAGTGACGAGAGCATGATTGAGAC

ACGCTGTGTTCTTAACTCGCACAGCACAGCTGAGACCACTCTTGATAGTT

TCTTCAGCAGAGCGGGATTAGTTGGAGAGATAGATCTCCCTCTTAAAGGC

ACAACTAACCCAAATGGTTATGCCAACTGGGACATAGATATAACAGGTTA

CGCGCAAATGCGTAGAAAGGTGGAGCTATTCACCTACATGCGCTTTGATG

CAGAGTTCACTTTTGTTGCGTGCACACCCACCGGGGAAGTTGTCCCACAA

TTGCTCCAATATATGTTTGTGCCACCTGGAGCCCCTAAGCCAGATTCCAG

GGAATCCCTCGCATGGCAAACCGCCACCAACCCCTCGGTTTTTGTCAAGC

TGTCAGACCCTCCAGCGCAGGTTTCAGTGCCATTCATGTCACCTGCGAGC

GCTTACCAATGGTTTTATGACGGATATCCCACATTCGGAGAACACAAACA

GGAGAAAGATCTTGAATATGGGGCATGTCCTAATAACATGATGGGCACGT

TCTCAGTGCGGACTGTAGGGACCTCCAAGTCCAAGTACCCTTTAGTGGTT

AGGATTTACATGAGAATGAAGCACGTTAGGGCGTGGATACCTCGCCCGAT

GCGTAACCAGAACTACCTATTCAAAGCCAACCCAAATTATGCTGGCAACT

CCATTAAGCCAACTGGTACCAGTCGTACAGCGATCACTACTCTTTAA

PCR Primer Sequence:
F6 (Homologous sequence to 5' flanking region of ORF7; start codon; Homologous sequence to EV71-VP1):

(SEQ ID NO: 17)
CGAATCGTCGGTTTGGAGGATTTATCCATAGTTCAATACGTTGGAAAGCC

AGTCAATCATGGGAGATAGGGTAGCAGATGTAA

R6 (Homologous sequence to 3' flanking region of ORF7; Homologous sequence to EV71-VP1):

(SEQ ID NO: 18)
AATTTTATATACAAAATAAAAACATACACCAGAAACGTTTTTAGTTTTTA

TTTCAATATTTAAAGAGTAGTGATCGCTGTACGACTGGTA

Transform the electrocompetent SW102 strain of E. coli containing VZV-7DRM BAC with the purified PCR product. The recombinant SW102 strains were screened and identified according to Example 2. After appropriate culture, VZV-7DRM-VP1 BAC was isolated and then co-transfected into ARPE cell with cre expression vector via electroporation. BAC was entirely excised from loxP sites at both ends of BAC, subsequently, the recombinant VZV-7DRM-VP1 virus was obtained. Monolayer ARPE cells were infected by recombinant virus and were cultured at 35° C. for 3-4 days. Then cells presented cytopathy. The activity of VP1 from was detected by EV71 specific sandwich ELISA in the culture supernatant from recombinant virus and centrifugal supernatant from cell lysis (after repeated frozen-thaw or sonificatoin). EV71 and VZV-7DRM serves as control. The results (table 3) show that the activity of VP1 was detected in ARPE cell infected by VZV-7DRM-VP1 virus. This suggests that VP1 is recombinated into VZV-7DRM virus. This example showed that VZV-7DRM can be used as vector to express foreign genes.

TABLE 3

Detection of activity of VP1 in recombinant VZV-7DRM-VP1 virus by sandwich ELISA

| type | EV71 activity detected by sandwich ELISA (OD) | |
|---|---|---|
| | culture supernatant | supernatant of cell lysis after sonification |
| VZV-7DRM | 0.049 | 0.025 |
| VZV-7DRM-P1 | 0.048 | 0.692 |
| EV71 | 2.774 | 2.537 |

Similar experiments demonstrated that VZV-7D can also be used as expression vector for expression of foreign proteins.

While the embodiments of the present invention have been described in details, one skilled in the art will understand that, according to the teaching of the disclosures, various modifications and substituents may be made to those details, without departing from the scope of the present invention. The whole scope of the invention are defined by the appended claims and any of their equivalents.

What is claimed is:

1. A vaccine against varicella and/or herpes zoster, comprising a varicella virus, and an excipient or carrier acceptable in vaccines, wherein the ORF7 of said varicella virus is entirely or partially deleted so that the resulting virus is unable to infect human skin or sensory ganglion, wherein the varicella virus is the varicella virus deposited in China General Microbiological Culture Collection Center, Institute of Microbiology Chinese Academy of Sciences, NO.1 West Beichen Road, Chaoyang District, Beijing 100101, China on Jul. 28, 2009 with deposit number CGMCC No.3207.

2. The vaccine according to claim 1, wherein said ORF7 is entirely or partially replaced by antibiotic resistance genes.

3. The vaccine according to claim 2, wherein said antibiotic resistance genes are selected from penicillin, streptomycin and kanamycin resistance genes.

4. A method of inducing an immune response against varicella and/or herpes zoster, comprising administering a prophylactic effective amount of the vaccine according to claim 1.

5. An immunogenic composition comprising a prophylactic effective amount of the vaccine according to claim 1.

* * * * *